United States Patent
Knöpfle et al.

(10) Patent No.: US 7,473,257 B2
(45) Date of Patent: Jan. 6, 2009

(54) BENDING PLIERS FOR PERFORATED BONE PLATES AND BENDING-PLIERS SYSTEM

(75) Inventors: Christian Knöpfle, Donaueschingen (DE); Frank Thorsten, Mühlheim an der Donau (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 590 days.

(21) Appl. No.: 10/758,925

(22) Filed: Jan. 16, 2004

(65) Prior Publication Data

US 2004/0176780 A1 Sep. 9, 2004

(30) Foreign Application Priority Data

Jan. 17, 2003 (DE) ................................. 103 01 692

(51) Int. Cl.
*A61B 17/60* (2006.01)
(52) U.S. Cl. ...................... 606/101; 606/105; 606/207; 72/380; 72/390.5; 81/419
(58) Field of Classification Search ............. 606/69–71, 606/99, 101, 104, 105, 207; 76/64; 81/300, 81/409, 419; 140/123; 433/4; 7/125; 72/409.01, 72/412–416, 390.5, 389.1, 389.2, 380; 59/7, 59/27; 411/474
See application file for complete search history.

(56) References Cited

U.S. PATENT DOCUMENTS

| | | | | | |
|---|---|---|---|---|---|
| 1,108,493 | A | * | 8/1914 | Federspiel | .................... 72/384 |
| 1,268,922 | A | * | 6/1918 | Bryan | ........................ 72/390.5 |
| 1,842,678 | A | * | 1/1932 | Kreuzeder | .................. 72/379.2 |
| 3,960,147 | A | * | 6/1976 | Murray | .......................... 606/75 |
| 4,038,755 | A | * | 8/1977 | Hernandez | ...................... 433/4 |
| 4,905,679 | A | * | 3/1990 | Morgan | ........................ 606/70 |
| 5,217,464 | A | * | 6/1993 | McDonald | .................. 606/107 |
| 5,651,283 | A | | 7/1997 | Runciman et al. | |
| 5,951,587 | A | | 9/1999 | Qureshi et al. | |
| 6,036,692 | A | * | 3/2000 | Burel et al. | .................... 606/61 |
| 6,960,211 | B1 | * | 11/2005 | Pfefferle et al. | ................ 606/69 |

FOREIGN PATENT DOCUMENTS

DE 29514830 2/1996

* cited by examiner

*Primary Examiner*—Eduardo C Robert
*Assistant Examiner*—James L Swiger, III
(74) *Attorney, Agent, or Firm*—Howard & Howard Attorneys, P.C.

(57) ABSTRACT

Bending pliers are described for perforated bone plates with two jaws movable relative to one another. A receiving jaw has two spaced receptacles for insertion into holes of a bone plate to be received. A pressure-exerting jaw comprises a pressure-exerting element which, when the bending pliers are actuated, cooperates with a received bone plate in a region between the two receptacles. The receptacles have an outside diameter which is variable along their axial extent in order to cooperate, preferably in a form-fitting manner, with different hole types.

13 Claims, 6 Drawing Sheets

BENDING PLIERS FOR PERFORATED BONE PLATES AND BENDING-PLIERS SYSTEM

CROSS-REFERENCE TO RELATED APPLICATION

The instant application claims priority to German Patent Application Serial Number 10301692.9, filed Jan. 17, 2003.

TECHNICAL FIELD

The invention relates to bending pliers for perforated bone plates and to a bending-pliers system comprising bending pliers and one or more bone plates.

BACKGROUND OF THE INVENTION

In surgical operations in the mid-face region for example, perforated bone plates are generally used to fix bones or bone fragments. It is frequently necessary here to adapt a bone plate to the contour of a bone or bone fragment. Such adaptation can be effected either by manual bending of the bone plate or by means of suitable bending pliers or a suitable pair of bending pliers. Thus, it is known to receive a bone plate with two separate bending pliers and to deform it by a relative movement between the two bending pliers.

The object on which the invention is based is to specify multifunctional bending pliers.

SUMMARY OF THE INVENTION

This object is achieved according to the invention by bending pliers for perforated bone plates which comprise two jaws movable relative to one another. A first jaw in the form of a receiving jaw has two spaced-apart receptacles with an axial extent for insertion into holes of a bone plate to be received. A second jaw in the form of a pressure-exerting jaw comprises a pressure-exerting (or counter-bearing) element which, when the bending pliers are actuated, cooperates with a received bone plate in a region between the two receptacles. The receptacles have an outside diameter which is variable in their axial extent in order to cooperate with different hole types, in particular different hole diameters.

The reception of the different bone plates preferably takes place in a form-fitting manner. For this purpose, the receptacles have, for example, an expediently circular or elliptical cross-section matched to the hole shape of the individual bone plates or, for example, a cross-section in the shape of an external hexagon. Other cross-sectional shapes are also conceivable, provided that a secure reception of the bone plates is ensured.

According to a preferred embodiment of the invention, the receptacles have an outside diameter which is smallest at the free ends of the receptacles and increases continuously in the direction of a bearing arrangement of the two jaws. The increase in the outside diameter preferably takes place in a stepped manner or else constantly in the mathematical sense, i.e. without bends. In the case of a stepped configuration of the outside diameter, preferably between two and five steps are provided. In the case of a constantly increasing outside diameter, the receptacles are preferably of conical design.

The receptacle pair can extend in different directions in relation to a pressure-exerting direction, i.e. in relation to that direction in which the pressure-exerting element transmits a force into a received bone plate. According to a first version of the invention, the receptacles extend substantially perpendicularly to the pressure-exerting direction. In this configuration, bending of a received bone plate takes place within the hole plane. According to a second version, the receptacles extend substantially parallel to the pressure-exerting direction. This means that a received bone plate is deformed out of the hole plane.

The pressure-exerting element, which transmits the pressure-exerting force into the bone plate, can have various designs. A peg-shaped pressure-exerting element with, for example, a cylindrical or conical shape is expedient. The cross-section of the pressure-exerting element can, to a very large degree, be freely chosen. Circular or drop-shaped cross-sections have proved advantageous in practice.

The arrangement of a peg-shaped pressure-exerting element in relation to the receptacles is chosen according to whether a received plate is to be bent in the hole plane or out of the hole plane. In the first case, in a pressure-exerting position of the bending pliers, i.e. in a position in which a pressure-exerting force can be transmitted into the bone plate, the receptacles and the peg-shaped pressure-exerting element run substantially parallel to one another. In the second case, i.e. when the bone plate is to be deformed out of the hole plane, the receptacle pair and the peg-shaped pressure-exerting element extend approximately perpendicularly to one another. Expediently, the axial extent of the receptacles corresponds approximately to the axial extent of the pressure-exerting element, i.e. the free ends of these components lie approximately on one plane.

A bending-pliers system according to the invention comprises, besides the bending pliers already explained, at least two types of bone plates, each with a different hole type. Thus, a first bone-plate type can have, for example, a hole diameter in the range between approximately 1 and 3 mm and a second bone-plate type can have a hole diameter of between approximately 3 and 6 mm. Additionally or alternatively, the bending-pliers system could have a bone plate with a hole type which differs from section to section.

The one or more bone plates of the bending-pliers system according to the invention can have a planar or a nonplanar form. Nonplanar bone plates with a single row of holes are preferred.

In principle, the distances between two holes can be freely chosen. Distances of between approximately 2 and 8 mm have proved expedient. It is particularly advantageous if the distances between each two holes of different types of bone plates are equal or are an integral multiple of one another. In the case of a bone plate with a hole type which differs from section to section, the distance between each two holes of a first region should be equal to or an integral multiple of the distance between each two holes of a second region.

BRIEF DESCRIPTION OF THE DRAWINGS

Further advantages and configurations of the invention emerge from the following description of preferred exemplary embodiments and the figures, in which.

DESCRIPTION OF A PREFERRED EMBODIMENT

Embodiments of bending pliers according to the invention and of a bending-pliers system according to the invention are described hereinbelow. In this particular example, the bending-pliers system according to the invention comprises two linear bone-plate types, each with a different hole diameter. The bending-pliers system could of course also comprise further or other bone-plate types or a single bone plate with regionally different hole diameters. Moreover, it should be noted that the receiving pegs of the bending pliers according to the invention described hereinbelow could be shaped differently than explained in the exemplary embodiment.

Figure 1:
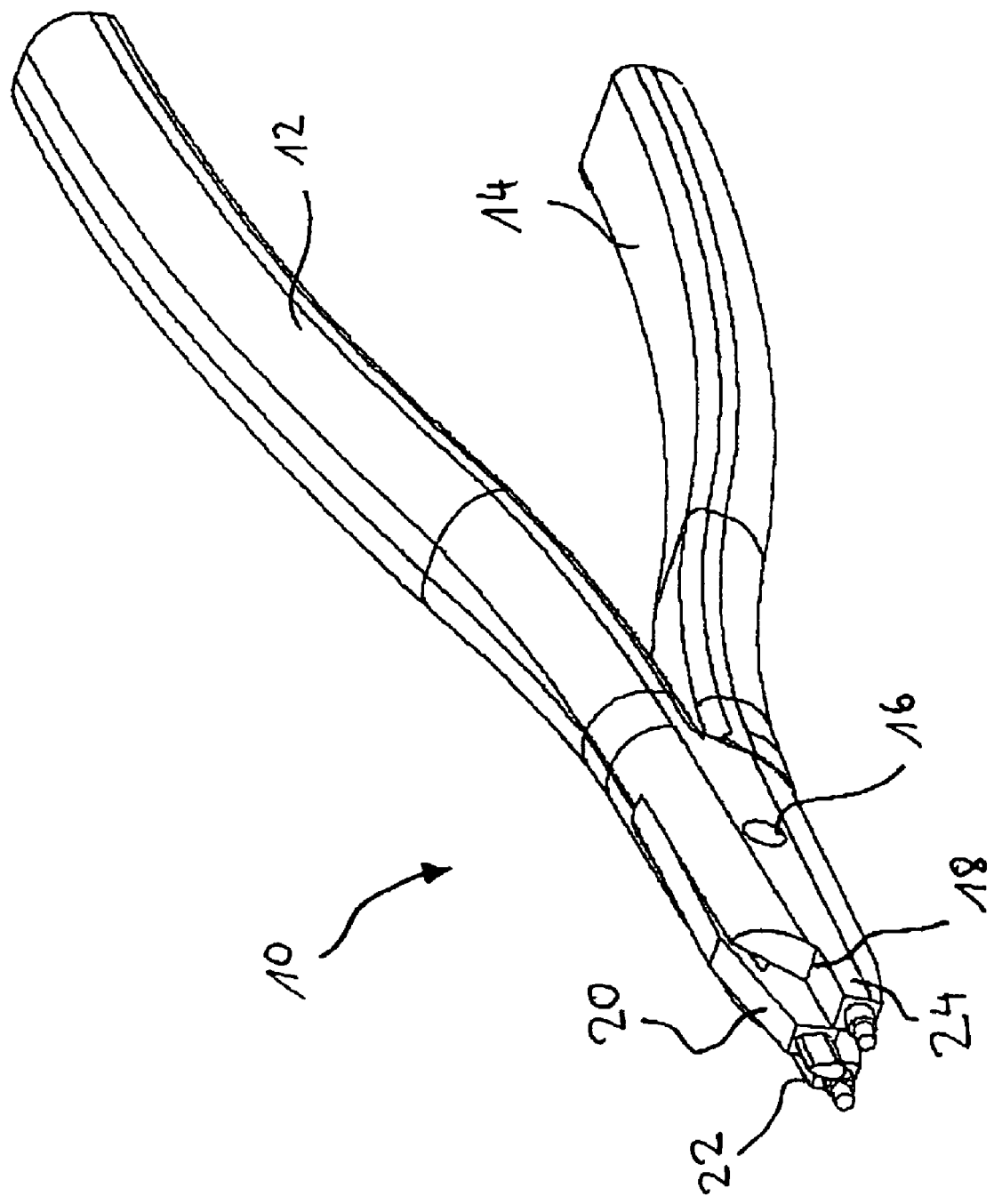
FIG. 1 shows a perspective view of bending pliers according to the invention.

FIG. 1 shows a perspective overall view of bending pliers 10 according to the invention. The bending pliers 10 comprise at one end two handles 12, 14 which have a common bearing arrangement 16. On the side of the bearing arrangement 16 opposite the handles 12, 14, the bending pliers 10 have two jaws 18, 20 movable relative to one another.

The jaw 18 functions as a receiving jaw for bone plates and is designed integrally with the handle 12. The jaw 20 functions as a pressure-exerting jaw and is designed integrally with the other handle 14. As can be seen in FIG. 1, the receiving jaw 18 has two receiving limbs 22, 24 spaced along an axis of rotation defined by the bearing arrangement 16. The pressure-exerting jaw 20 is arranged in a region between these two receiving limbs 22, 24. This means that, when the bending pliers 10 are actuated, the pressure-exerting jaw 20 moves between the two receiving limbs 22, 24.

Figure 2:
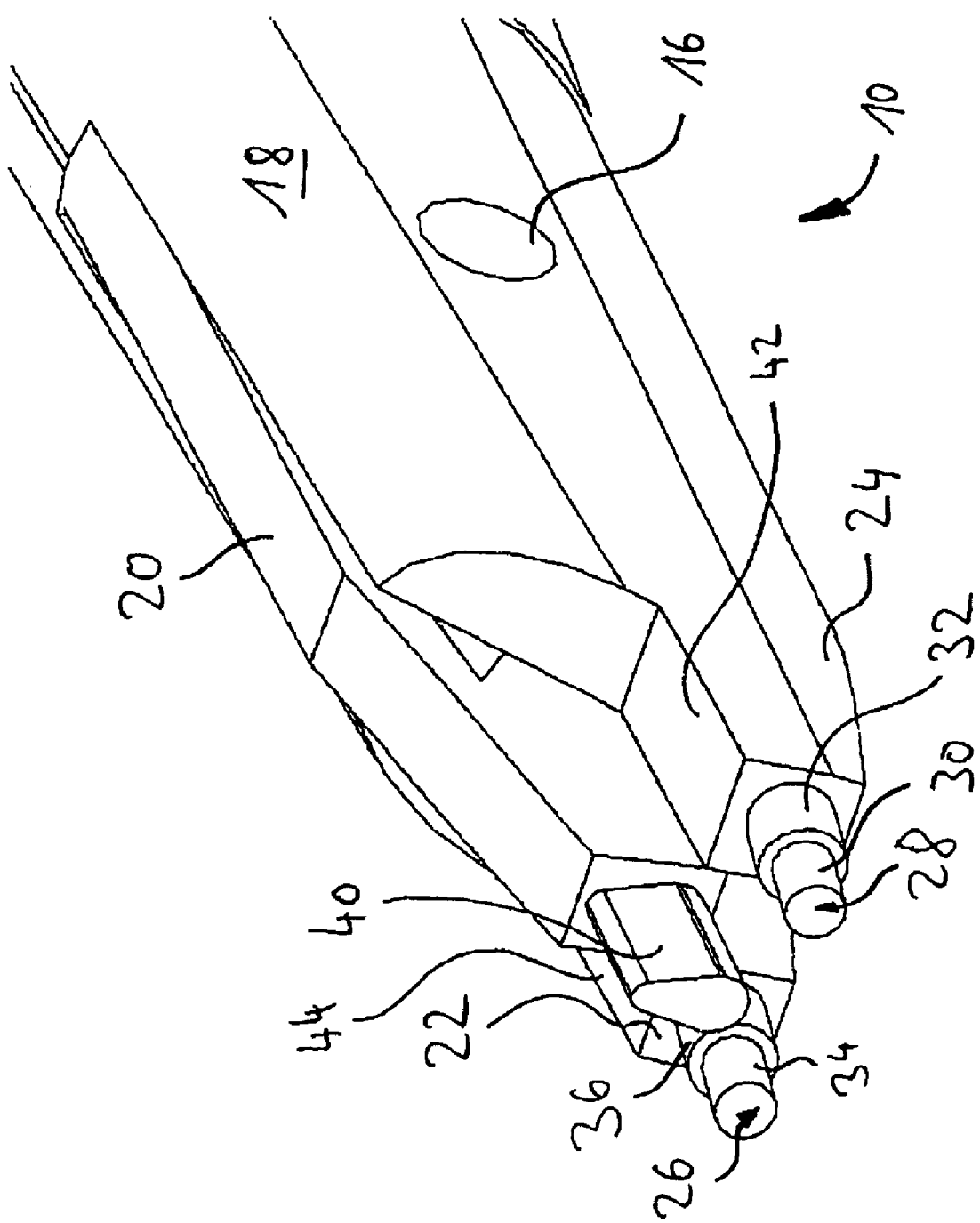
FIG. 2 shows an enlarged, perspective view of the two cooperating jaws of the bending pliers illustrated in FIG. 1.

In FIG. 2, the front end of the bending pliers according to the invention as shown in FIG. 1 is illustrated in enlarged form. Clearly visible are the two receptacles 26, 28 of the receiving jaw 18 which are peg-shaped in this particular example. A first receiving peg 26 forms an extension of the receiving limb 22 on the left in FIG. 2 and a second receiving peg 28 forms an extension of the receiving limb 24 on the right in FIG. 2. The two receiving pegs 26, 28 are thus carried by different receiving limbs 22, 24 and are consequently offset from one another (as are the receiving limbs 22, 24) in the direction of an axis of rotation defined by the bearing arrangement 16. The two receiving pegs 26, 28 are mutually spaced by approximately 5 mm.

Starting from a free end, facing away from the bearing arrangement 16, each of the two receiving pegs 26, 28 has a continuously increasing outside diameter. In the particular example illustrated in FIG. 2, the outside diameter of each of the two receiving pegs 26, 28 increases in a stepped manner. To be more precise, each of the receiving pegs 26, 28 comprises two cylindrical regions 30, 32, 34, 36 of different outside diameter. The outside diameter of the front cylindrical region 30 (on the left in FIG. 2) of the receiving peg 28 corresponds to the outside diameter of the front cylindrical region 34 of the receiving peg 26. The same applies to the respective outside diameters of the rear cylindrical regions 32, 36 (on the right in FIG. 2).

In a departure from the situation illustrated in FIG. 2, the receiving pegs 26, 28 could also have a constantly (e.g. conically) increasing outside diameter.

The pressure-exerting jaw 20 has at its front end a cylindrical pressure-exerting element 40 with a drop-shaped cross-section. In the illustration according to FIG. 2, the pressure-exerting element 40 runs substantially parallel to the two receiving pegs 26, 28 of the receiving jaw 18. This means that the receiving pegs 26, 28 extend substantially perpendicularly to a pressure-exerting direction defined by the pressure-exerting element 40. As will become clear from the following statements, this means that the bending pliers 10 of the exemplary embodiment permits the deformation of a received bone plate in the hole plane.

If bending of a bone plate out of the hole plane were to be necessary, the bending pliers illustrated in FIG. 1 would have to be modified slightly. In this case, the receiving pegs 26, 28 would have to be rotated 90° clockwise in FIG. 2. For this purpose, a corresponding mechanism which permits a change of the position of the receiving pegs 26, 28 could be provided. As an alternative to this, it would be possible to arrange the receiving pegs 26, 28, for example, on the free surfaces 42, 44 of the receiving limbs 22, 24 in such a way that they are upright in FIG. 2. In this case, it would be additionally necessary to displace the pressure-exerting element 14 slightly to the right in FIG. 2.

Figure 3:
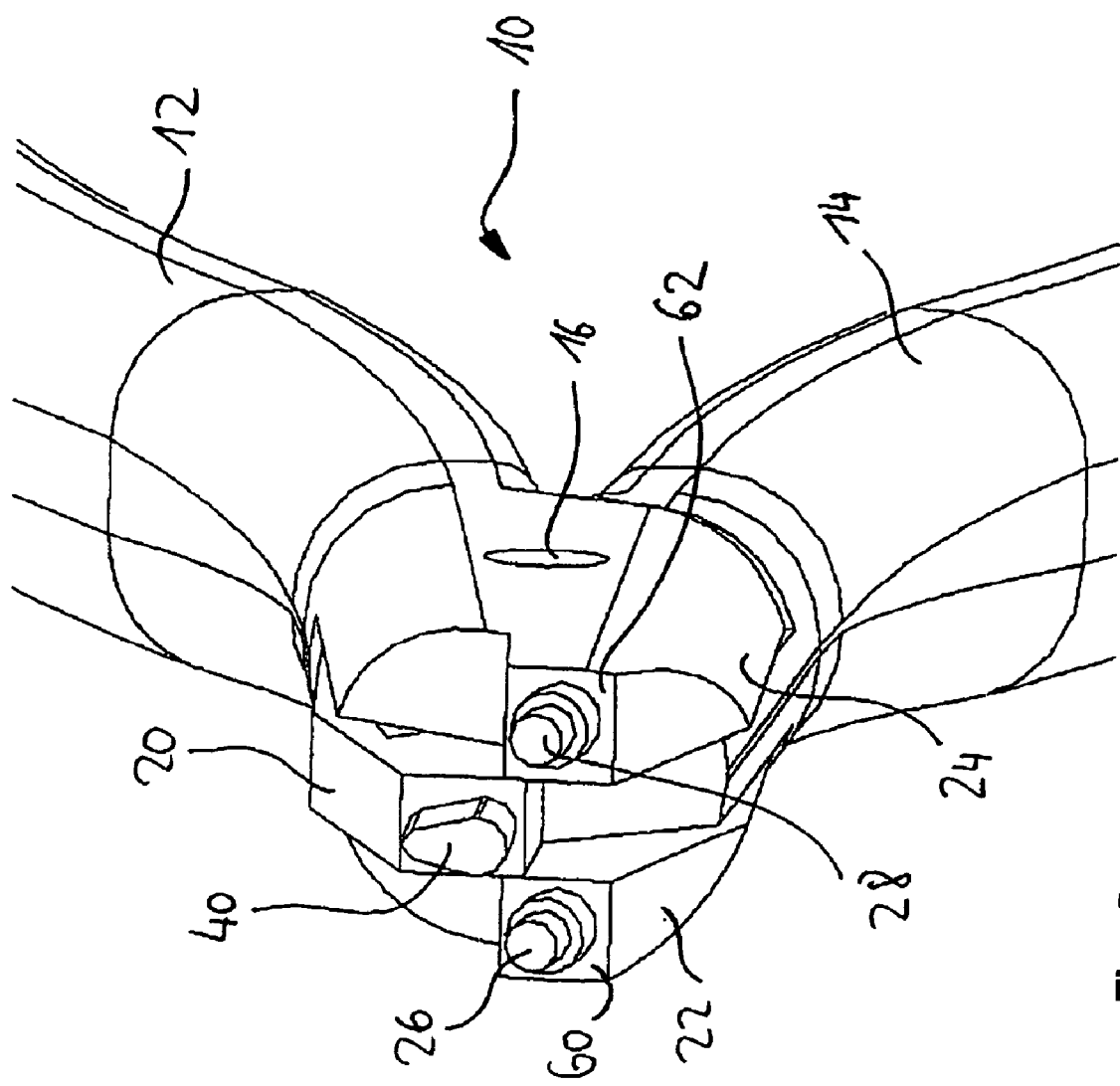
FIG. 3 shows a perspective view of the region illustrated in FIG. 2 from another viewing angle.

FIG. 3 shows a view of the bending pliers 10 according to the invention similar to the view of FIG. 2 but from another viewing angle.

Figure 4:
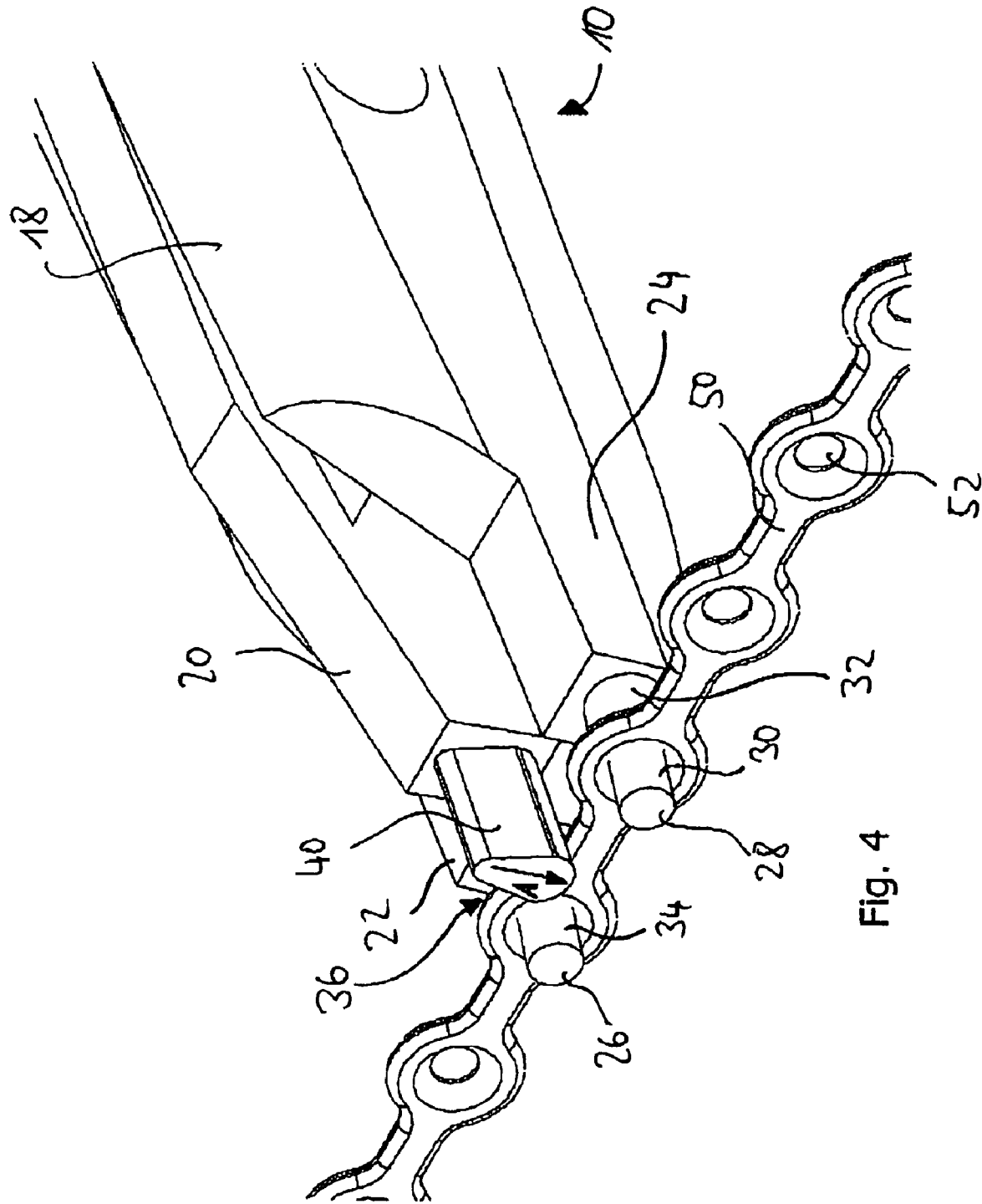
FIG. 4 shows the bending of a bone plate with a small hole diameter using the bending pliers according to FIG. 1.

FIG. 4 shows the bending pliers 10 according to FIGS. 1 to 3 with a received linear bone plate 50 of a first type. The bone plate 50 has a plurality of linearly arranged holes 52 of a first diameter. The diameter of the holes 52 is chosen to be slightly greater than the outside diameter of the front cylindrical regions 30, 34 of the receiving pegs 26, 28. In addition, the centre-to-centre distance of two adjacent holes of the bone plate 50 corresponds to the centre-to-centre distance of the two receiving pegs 26, 28.

The bone plate 52 can be pushed onto the front cylindrical regions 30, 34 until the bone plate 52 comes to bear against an end face, facing the bone plate 52, of the rear cylindrical regions 32, 36 of greater diameter (the cylindrical region 36 of the receiving peg 26 is concealed in FIG. 4 by the bone plate 50).

It can be clearly seen from FIG. 4 that, when the bending pliers 10 are actuated, the pressure-exerting element 40 cooperates with the received bone plate 50 in a region between the two receiving pegs 26, 28. This cooperation takes place in a pressure-exerting direction indicated by the arrow A. The pressure-exerting direction is perpendicular to the axial extent of the receiving pegs 26, 28 and to that plane in which the holes 52 of the bone plate 50 are arranged. When the bending pliers 10 are actuated, the bone plate 50 is therefore deformed in the hole plane. This means that the holes of the deformed bone plate lie in the same plane as the holes of the bone plate before deformation.

Figure 5:
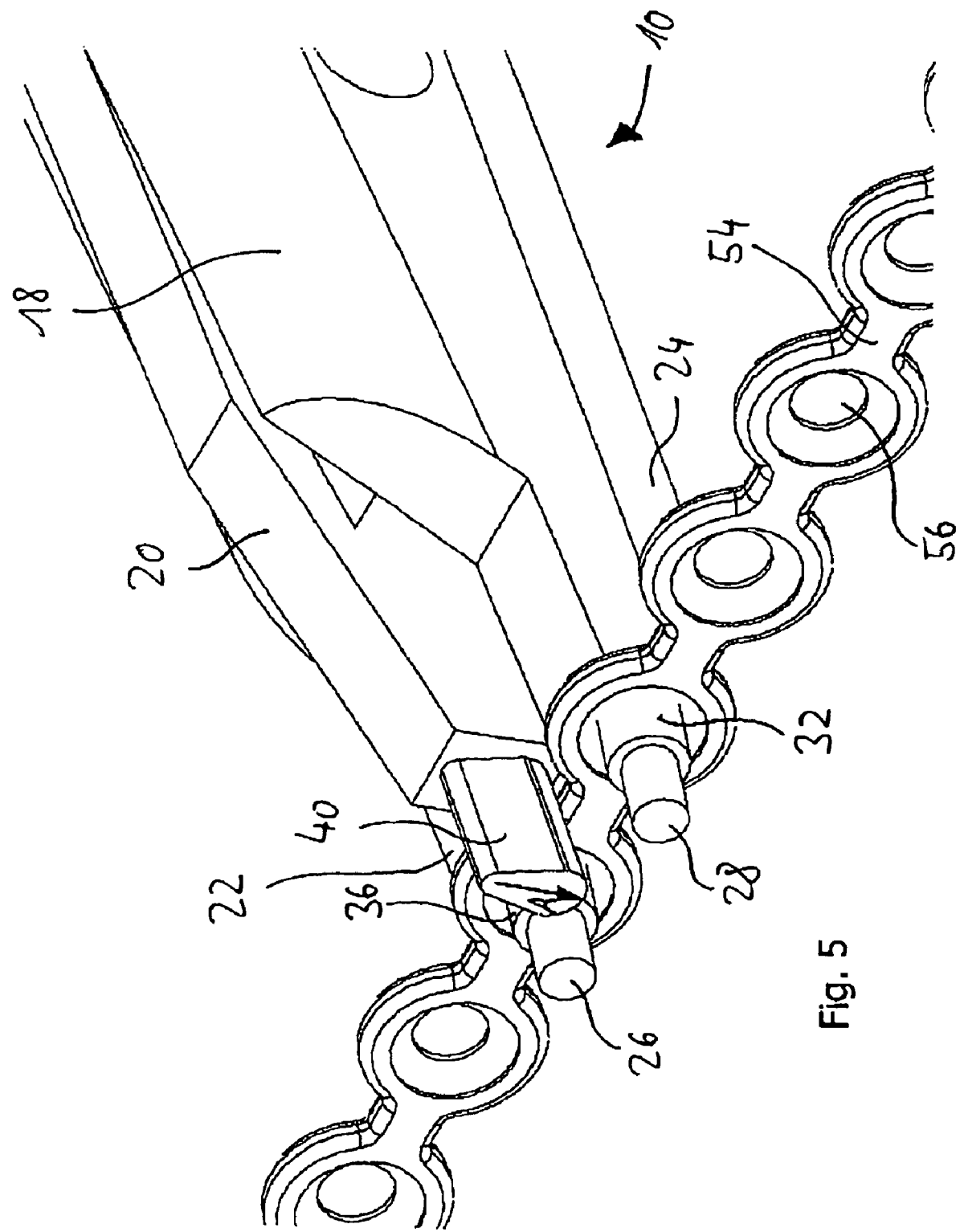
FIG. 5 shows the bending of a bone plate with a large hole diameter using the bending pliers according to FIG. 1.

FIG. 5 shows a view similar to FIG. 4. In the case illustrated in FIG. 5, the receiving pegs 26, 28 of the bending pliers 10 receive a linear bone plate 54 of a second type. The bone plate 54 of the second type has a plurality of holes 56 with a greater diameter than the holes 52 of the bone plate 50 of the first type illustrated in FIG. 4.

To be more precise, the holes 54 have a diameter which is slightly greater than the outside diameter of the rear cylindrical regions 32, 36 of the receiving pegs 26, 28. The centre-to-centre hole distance of the bone plate 54 corresponds to the centre-to-centre hole distance of the bone plate 50 according to FIG. 4. The bone plate 54 can be pushed onto the rear cylindrical regions 32, 36 until the rear side of the bone plate 54 comes to bear against the end faces 60, 62 of the receiving limbs 22, 24 illustrated in FIG. 3.

Figure 6:
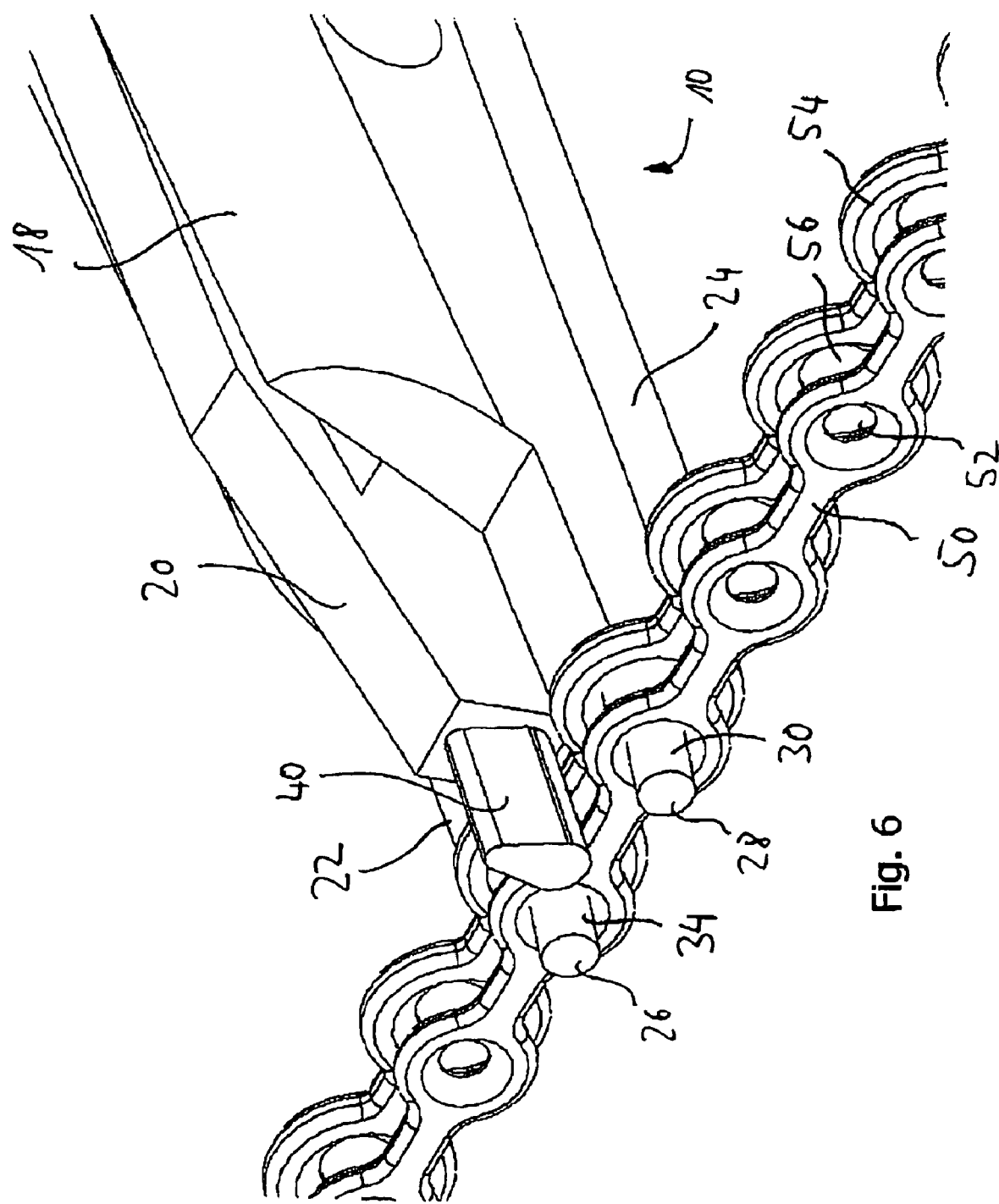
FIG. 6 shows the bending pliers according to FIG. 1 with two different bone-plate types.

FIG. 6 shows a view of the bending pliers 10 similar to FIGS. 4 and 5. In the case illustrated in FIG. 6, the receiving pegs 26, 28 receive the bone plate 50 according to FIG. 4 and at the same time the bone plate 54 according to FIG. 5. This means that the two bone plates 50, 54 can be deformed in a single working step and to the same extent.

From the foregoing explanations, it has become clear that the bending pliers 10 according to the invention can be used to deform bone plates of different hole diameters. A change of bending pliers during a surgical operation can thereby be avoided in many cases. In addition, the bending pliers according to the invention allow the simultaneous bending of bone plates of different hole diameter.

The above-described embodiment of the invention is intended to be an example of the present invention, and alterations and modifications may be effected thereto, by those of ordinary skills in the art, without departing from the scope of the invention which is defined by the claims appended hereto.

The invention claimed is:

1. Bending pliers for perforated bone plates, comprising:
   two jaws movable relative to one another, including a receiving jaw having two spaced-apart peg members at a fixed distance to one another with an axial extent and having a first circumference operable for insertion through holes of a substantially planar bone plate to be received, the peg members having an outside diameter which is variable along their axial extent in order to cooperate with different hole types; and
   a pressure-exerting jaw comprising a pressure-exerting element which, when the bending pliers are actuated, cooperates with a received bone plate in a region between the two peg members, wherein the pressure-exerting element is of a substantially peg-shaped design and has a second circumference inoperable to engage the holes of the bone plate;
   wherein the two peg members of the receiving jaw are fixed along a single axis;
   wherein the pressure exerting jaw is selectively operable to move transverse to the single axis.

2. The bending pliers according to claim 1, wherein the peg members are designed for form-fitting cooperation with different hole types.

3. The bending pliers according to claim 1, wherein the peg members have an outside diameter which increases in a stepped or continuous manner starting from free ends of the peg members.

4. The bending pliers according to claim 1, wherein the peg members extend substantially perpendicularly to a pressure-exerting direction.

5. The bending pliers according to claim 1, wherein the peg members extend substantially parallel to a pressure-exerting direction.

6. The bending pliers according to claim 1, wherein, in a pressure-exerting position, the two peg members and the peg-shaped pressure-exerting element extend substantially parallel or perpendicularly to one another.

7. The bending pliers according to claim 1, wherein the axial extent of the peg members corresponds approximately to the axial extent of the pressure-exerting element.

8. A bending-pliers system comprising:
   bending pliers having two jaws movable relative to one another, including a receiving jaw having two spaced-apart peg members at a fixed distance to one another with an axial extent and having a first circumference operable for insertion through holes of a substantially planar bone plate to be received;
   a pressure-exerting jaw comprising a pressure-exerting element which, when the bending pliers are actuated, cooperates with a received bone plate in a region between the two peg members, the peg members having an outside diameter which is variable along their axial extent in order to cooperate with different hole types, wherein the pressure-exerting element is of a substantially peg-shaped design and has a second circumference inoperable to engage the holes of the bone plate; and
   at least two types of substantially planar bone plates, each with a different hole type, or a substantially planar bone plate with holes of different types;
   wherein the two peg members of the receiving jaw are fixed along a single axis;
   wherein the pressure exerting jaw is selectively operable to move transverse to the single axis.

9. The bending-pliers system according to claim 8, wherein the bone plates are bone plates with a single row of holes.

10. The bending-pliers system according to claim 8, wherein the distances between each two holes of different types of bone plates or of a bone plate with regionally different hole types are equal or are an integral multiple of one another.

11. Bending-pliers with jaws that are moveable relative to one another, comprising:
    a first jaw having two spaced-apart peg members at a fixed distance to one another, the peg members of the first jaw having a first circumference operable for insertion through holes of a substantially planar bone plate to be received, the peg members each having a free end and an outside diameter that increases starting from the free end; and
    a second jaw supporting a counter-bearing element that cooperates upon actuation of the bending pliers with a received bone plate in a region between the two peg members of the first jaw, wherein the counter-bearing element is of a substantially peg-shaped design and has a second circumference inoperable to engage the holes of the bone plate;
    wherein the first and second jaws are moveable relative to one another;
    wherein the two peg members of the receiving jaw are fixed along a single axis;
    wherein the pressure exerting jaw is selectively operable to move transverse to the single axis.

12. The bending pliers of claim 11, wherein the peg members are designed to form-fittingly cooperate with bone plate holes of different diameters.

13. The bending pliers according to claim 11, wherein the peg members extend substantially perpendicularly to a direction in which the counter-bearing element is moved when the bending-pliers are actuated.

* * * * *

UNITED STATES PATENT AND TRADEMARK OFFICE
CERTIFICATE OF CORRECTION

PATENT NO. : 7,473,257 B2 Page 1 of 1
APPLICATION NO. : 10/758925
DATED : January 6, 2009
INVENTOR(S) : Christian Knopfle It is certified that error appears in the above-identified patent and that said Letters Patent is hereby corrected as shown below:

On the Title Page of the patent in item 75 the Inventors section, please rearrange the first and last name of the inventor Frank Thorsten, so the name reads Thorsten Frank.

Signed and Sealed this

Tenth Day of August, 2010

David J. Kappos
*Director of the United States Patent and Trademark Office*